United States Patent
Halla et al.

(10) Patent No.: US 7,306,621 B1
(45) Date of Patent: Dec. 11, 2007

(54) HEAT TRANSFER CONTROL FOR A PROSTHETIC RETINAL DEVICE

(75) Inventors: Brian L. Halla, Saratoga, CA (US); Ahmad Bahai, Lafayette, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 473 days.

(21) Appl. No.: 10/995,047

(22) Filed: Nov. 19, 2004

(51) Int. Cl.
 *A61F 7/12* (2006.01)
 *A61F 9/08* (2006.01)
(52) U.S. Cl. .............................. 607/113; 606/21; 607/96
(58) Field of Classification Search ................. 607/96, 607/98, 99, 113; 606/20–23
See application file for complete search history.

(56) References Cited

U.S. PATENT DOCUMENTS 4,483,341 A * 11/1984 Witteles ..................... 606/21
6,248,126 B1 * 6/2001 Lesser et al. ............... 607/113
6,629,990 B2 * 10/2003 Putz et al. .................. 607/113

OTHER PUBLICATIONS

Mohan Yegnashankaran, U.S. Appl. No. 10/218,836, filed Oct. 28, 2002 (not attached).
Joseph Montalbo, U.S. Appl. No. 10/886,787, filed on Jul. 7, 2004 (not attached).
USC News Service, *Center of Attention* (Oct. 1, 2003) <http://www.usc.edu/uscnews/stories/9301.html>.
Tim Stephens, *New Engineering Center Focuses on Implantable Prosthetics*, UC Santa Cruz Currents Online, (Oct. 6, 2003) <http://www.ucsc.edu/currents/03-04/10-06/biomimetics.html>.
National Science Foundation, Division of Engineering Education & Center Program Areas (last modified Feb. 24. 2004).
Victor Rudometov et al., *Peltier coolers* <http://www.digit-life.com>.
C. Shafai et al., *A Micro-Integrated Peltier Heat Pump for Localized On-Chip Termperature Control*, CCECE (1996) pp. 88-91.
A. Foucaran et al., *Flash evaporated layers of $(Bi_2Te_3$-$Bi_2Se_3)$ (N) and $(Bi_2Te_3Sb_2Te_3)(P)$ used as Micro-Module-Peltier*, 16th International Conference on Thermoelectrics (1997) pp. 163-166.

* cited by examiner

*Primary Examiner*—Roy D. Gibson
(74) *Attorney, Agent, or Firm*—Darby & Darby PC; John W. Branch

(57) ABSTRACT

A method for controlling heat dissipated from a prosthetic retinal device is described. A heat transfer device employs the Peltier heat transfer effect to cool the surface of the retinal device that faces the retina by dissipating/transferring collected heat away from the retina and towards the iris or front of the eye. According to one embodiment, a heat pump is formed in a second substrate on the retinal device. The heat pump is controlled by a temperature sense device that activates the heat pump, when a first predetermined temperature limit is exceeded. The temperature sense device deactivates the heat pump, when a temperature of the retinal device drops below a second predetermined temperature. According to another embodiment, a supply current of the retinal device may pass through the heat pump and a direction of heat transfer by the heat pump can be reversed, when the first predetermined temperature is exceeded.

21 Claims, 7 Drawing Sheets

HEAT TRANSFER CONTROL FOR A PROSTHETIC RETINAL DEVICE

FIELD OF THE INVENTION

The present invention relates to eye prosthetics, and, in particular, to a method for controlling heat transfer from a prosthetic retinal device to eye tissue.

BACKGROUND

Various diseases, physical trauma, and birth defects can result in the destruction or impaired functionality of rod and cone cells in the retina, which are the primary mechanism for converting incident light into electro-chemical signals that can be interpreted as sight by the brain. Generally, loss of this functionality can not be mitigated by conventional surgical or pharmacological methods.

A prosthetic retinal device could be used to restore visual perception to a person suffering from damage to the retina due to birth defects, physical trauma, and/or disease such as retinitis pigmentosa, macular degeneration, and the like. Some birth defects, trauma, or disease can cause destruction of the rods and cones in the retina, but leave other retina cells such as ganglion cells largely intact. Consequently, the application of an electrical signal to these other cells in the retina can still enable the perception of light even if the rod and/or cone cells are impaired or absent. In the retina, ganglion cells translate electrical stimulation into electro-chemical messages which are subsequently communicated to the visual cortex of the brain through the optic nerve.

However, at least because of operational constraints such as intra-ocular temperature and/or pressure, physical size, physical contact with the retina, and power supply limitations, the resolution of electrical signals provided by a prosthetic retinal device may be limited. Thus, it is with respect to these considerations and others that the present invention has been made.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description of the Invention, which is to be read in association with the accompanying drawings, wherein.

DETAILED DESCRIPTION

Figure 1:
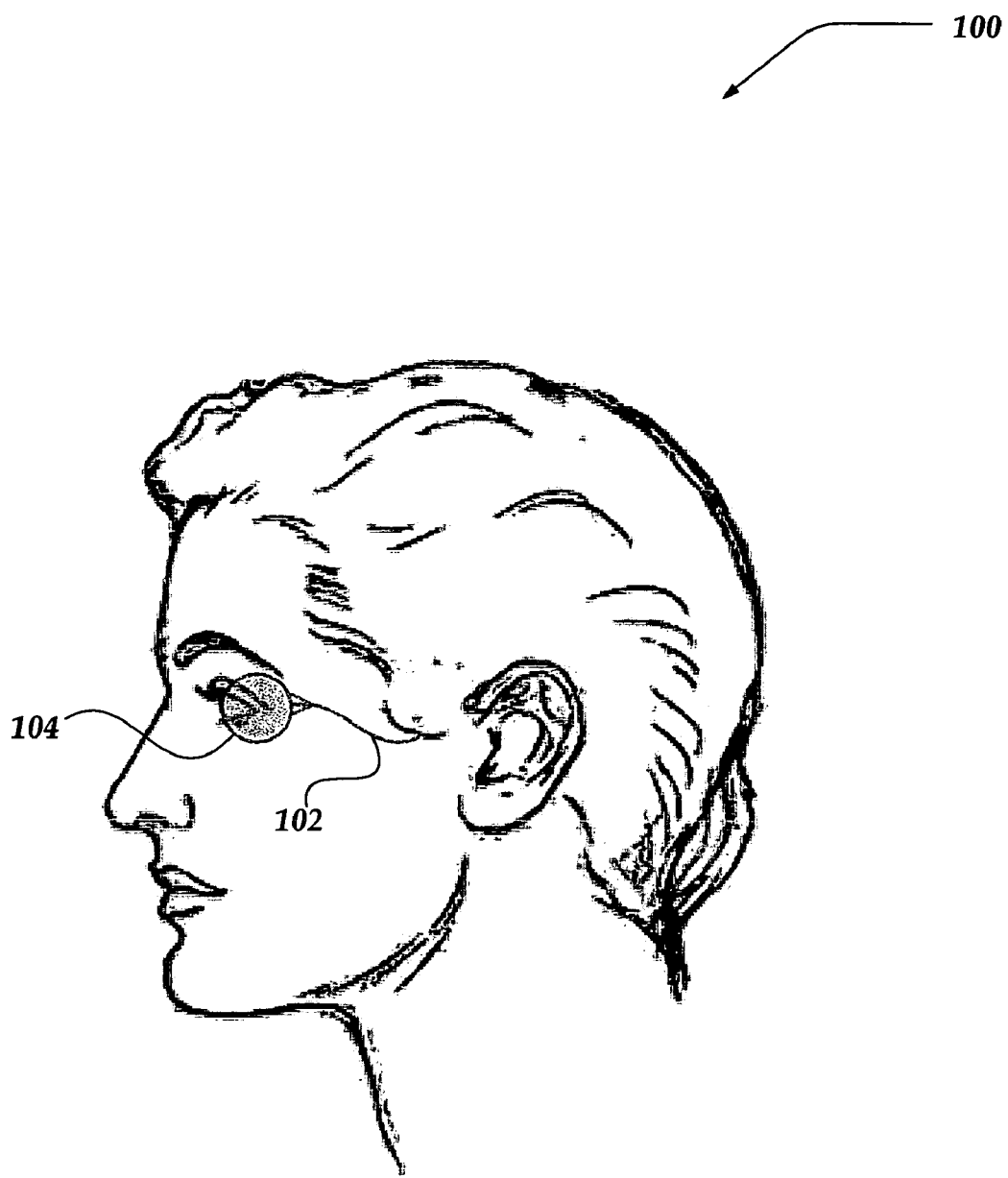
FIG. 1 illustrates a plan view of a human head.

The present invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods or devices. Accordingly, the present invention may take the form of an entirely hardware embodiment or an embodiment combining software and hardware aspects. The following detailed description is, therefore, not to be taken in a limiting sense.

Briefly stated, the present invention relates to a method and apparatus for a heat transfer device adapted for implementation with a prosthetic retinal device. In different embodiments, this prosthetic retinal device can be positioned on the surface of the retina (epiretinal), within the layers of the retina tissue (subretinal), or suspended within the eye at some distance away from the retina.

The prosthetic retinal device can imitate at least some of the operations of rod and cone cells such as providing electrical stimulation of ganglion cells in response to incident light. Generally, the prosthetic retinal device receives incident light information from a separate (or integrated) camera or sensor and translates this information into at least one electrical signal that is provided to and recognizable by ganglion cells in the retina. Also, by generating multiple electrical signals, a retinal device can provide a plurality of stimulation points (pixels of resolution) that can be interpreted by the brain as a form of sight.

The electrical signals provided by a prosthetic retinal device can be converted into electrochemical signals by ganglion cells and other underlying tissue structures for communication to the brain's visual cortex. These electrochemical signals are carried via the optic nerve to the brain for interpretation as sight. However, since the intra-ocular temperature is generally less than the normal body temperature of 98.6 degree Fahrenheit, it is possible that a relatively small build-up of heat in a prosthetic retinal device could jeopardize its chronic implantation. In particular, an elevated intraocular temperature caused by heat build up in a retinal device can erode the normal functionality of cells/tissue in the eye, increase the risk of an infection, and induce the immune system to respond with one or more defense mechanisms such as a fever, and the like. The inventive heat transfer device preserves intra-ocular temperature by enabling a prosthetic retinal device to dissipate heat away from retinal tissue/cells.

The inventive arrangement of components for dissipating/transferring heat generated at least in part by a prosthetic retinal device enables more power to be employed by the device without substantially deleterious results. For example, a prosthetic retinal device that employs more power to provide a higher resolution (multiple electrical signals for multiple pixels) without substantially increasing the heat dissipated to the retina at the point of implantation can do so without causing a substantial increase various risk factors.

One aspect of the present invention utilizes a heat transfer device based on the Peltier heat transfer effect to cool the retina or "back" side of the prosthetic retinal device by dissipating heat towards the pupil or "front end" of the eye. Typically, heat dissipated towards the pupil end of the eye may be more easily transferred outside of the body than heat that is dissipated towards the retina or "back" side of the eye.

Generally, the temperature gradient between the vitreous humor (fluid inside the eyeball) and the outside environment is larger than a temperature difference between the vitreous humor and the retina tissue.

In one embodiment, a Peltier based heat transfer device is formed in a second substrate on the surface of the prosthetic retinal device that faces away from the retina and towards the pupil. One aspect of the invention provides for a temperature sense circuit that can activate the heat transfer device, if a predetermined temperature is exceeded.

According to another embodiment, a supply current for a prosthetic retinal device may also pass through the heat transfer device and transfer of heat is subsequently controlled by reversing this supply current, if a predetermined temperature is exceeded.

While some embodiments may be implemented in a prosthetic retinal device, the invention is not so limited. For example, the inventive heat exchanger may be employed with a cortical implant device, a spinal implant device, and the like. Furthermore, the invention may be implemented in any electrical, mechanical, and electromechanical implant device, such as an artificial heart pump, a pacemaker, an insulin pump, and the like. It is understood that the invention may be implemented in virtually any implantable medical device where it is desirable to control heat dissipation of the device in situ.

Operating Environment

FIG. 1 illustrates human head 100, where the present invention may be implemented. Human head 100 includes, in addition to usual features such as ears, mouth, nose, and the like, eyeball 104 and optic nerve 102.

Eyeball 104 resides in an ocular cavity and is connected to the brain through optic nerve 102. Optic nerve 102 receives electrochemical signals representing visual information from ganglion cells in eyeball 104 to special regions of the thalamus and visual cortex in the brain. Optic nerve 102 also carries electrochemical signals from the brain to the eye.

Figure 2:
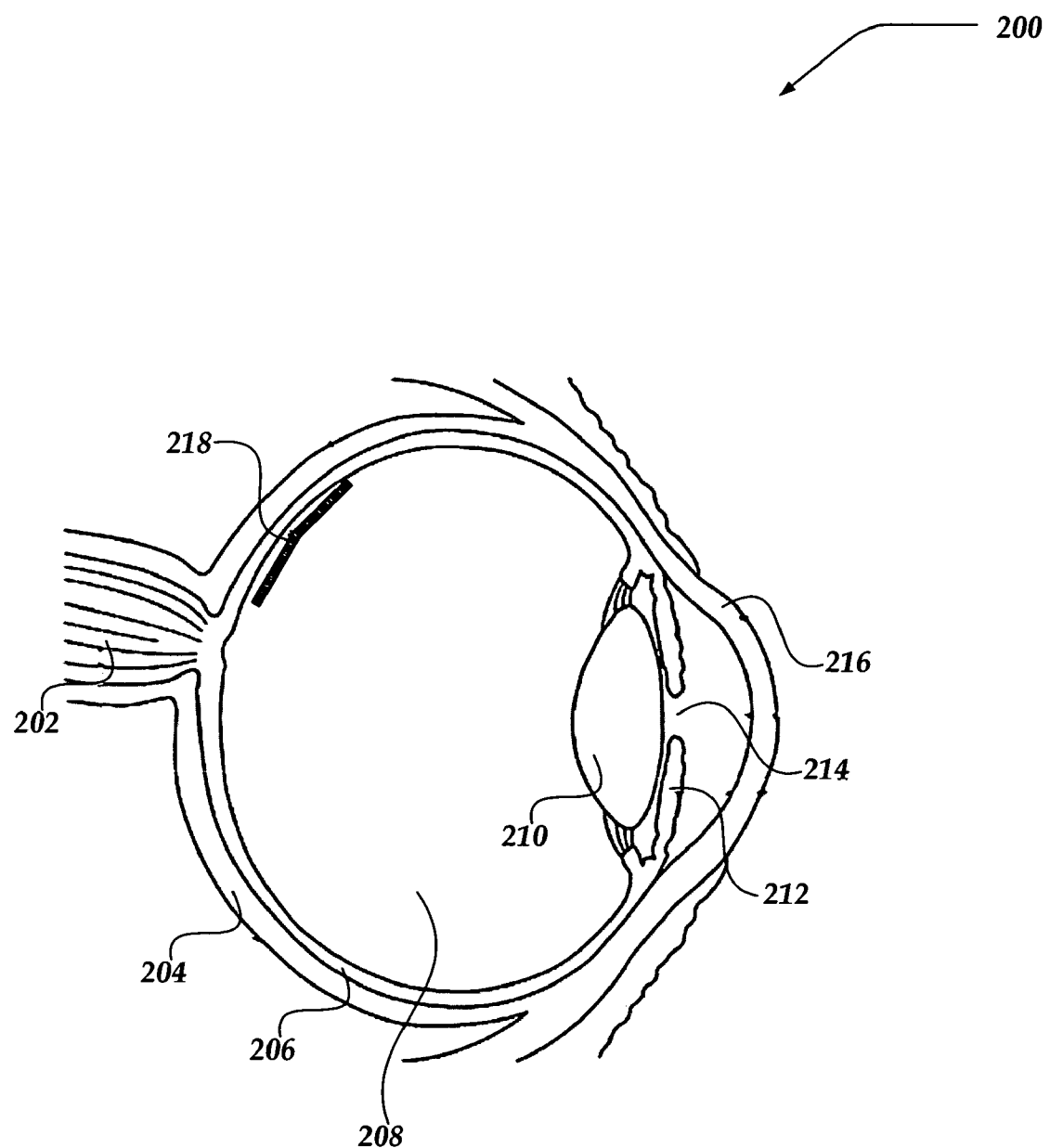
FIG. 2 shows a cut-away view of an eye with an epiretinal prosthetic device.

FIG. 2 illustrates eye 200 with epiretinal device 218. As shown, eye 200 includes at least optic nerve 202, sclera 204, retina 206, vitreous humor 208, lens 210, iris 212, pupil 214, cornea 216, and epiretinal device 218 disposed on the retina.

Optic nerve 202 is a bundle of about a million nerves that carry electrochemical signals corresponding to visual information from ganglion cells in retina 206 to the brain. Sclera 204 a white, non-transparent tissue, surrounds cornea 216 and provides protection to delicate inner structures of eye 200.

Retina 206 is disposed on an inner back wall of eye 200. Retina 206 includes several layers of specialized cells such as rods and cones, ganglion cells, optic nerve fibers, and the like. Rods and cones are photoreceptor cells in a bacillary layer that receives incident light through iris 212 and lens 210, and generate electrochemical signals in response to the received light. Typically, a human eye includes approximately six to seven million cones which can sense at least one of a red, blue, and green color. In contrast, the rods are far more numerous in a human eye than cones, about 120 million. While not color sensitive, the rods enable sight under dark, or scotoptic conditions. As mentioned above, diseases such as retinitis pigmentosa, macular degeneration, and the like may lead to damage of the retina layer that includes the rods and cones. In a healthy eye, the electrochemical signals generated by the rods and cones is captured by the ganglion cells in a different layer and transmitted to optic nerve fibers. Optic nerve fibers, distributed throughout retina 206, concentrate in one region and form optic nerve 202 connecting eye 200 to the brain.

Vitreous humor 208 is a gelatinous, clear liquid that fills the inner space of eye 200 surrounded by retina 206 and lens 210. Vitreous humor 208 enables the preservation of a round shape for eye 200, and helps maintain an inner temperature of eye 200 slightly below a body temperature. Vitreous humor 208 is also critical in maintaining intra-ocular pressure.

Lens 210 is an internal focusing element of eye 200. Lens 210 controls about one third of a refraction of light that enters eye 200. Lens 210 is curved on both sides and attached to ciliary muscle at its top and bottom. A contraction and expansion of the ciliary muscle in response to a signal from the brain enables lens 210 to alter its shape and thereby a focus of eye 200. Lens 210 comprises soft material that allows the alteration of its shape, also called accommodation. In addition to controlling the focus of eye 200, lens 210 also controls the refraction of incoming light by absorbing particular wavelengths more than others.

Iris 212 is located on the outside of lens 210 and is made of very fine muscular tissue. Iris 212, which gives the eye its color, has a substantially round hole in its center. The hole is pupil 214. Pupil 214 controls an amount of light that enters eye 200 through lens 210. A size of pupil 214 is managed by contraction and expansion of the muscular tissue of iris 212. The size of pupil 214 changes based, in part, on an ambient light level. A response of pupil 214 is partially based on a stimulation of rods and cones of retina 206.

Cornea 216 is a clear tissue covering a front part of eye 200 including iris 212. Cornea 216 is a main source of refraction (about two third). Cornea 216 does not include any blood vessels, and is made of five clear layers of epithelium. Cornea 216's main task is to protect the eye against injuries and to provide a barrier against infection.

Epiretinal device 218 can be arranged to provide electrical, mechanical, electromechanical, and the like, stimulation to ganglion cells of retina 206. Epiretinal device 218 may also include electrical circuitry that is arranged to receive light information from a camera, photoelectric sensor, and the like, determine characteristics of electrical signals to be generated in response to the received information and provide stimulation to the ganglion cells in the form of electrical signals, mechanical stimulation, or some combination of both electrical signals and mechanical stimulation.

Epiretinal device 218 may be manufactured employing a flexible semiconductor material which enables the device to have a curved structure that is suited for implantation in the eye. Although not shown, in addition to placement on the anterior surface of the retina, epiretinal device 218 may be positioned in the layers of the retina, or suspended in vitreous humor 208 near the anterior surface of the retina, and the like.

System and Apparatus

Figure 3A:
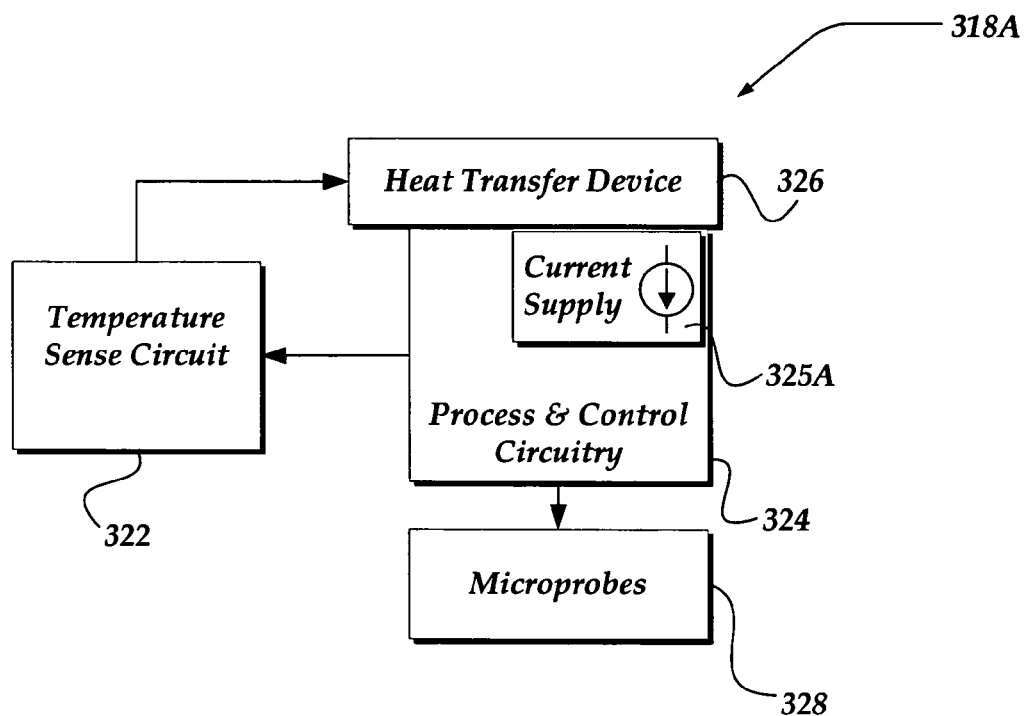
FIGS. 3A and 3B illustrates a block diagram of a epiretinal prosthetic device.
Figure 3B:
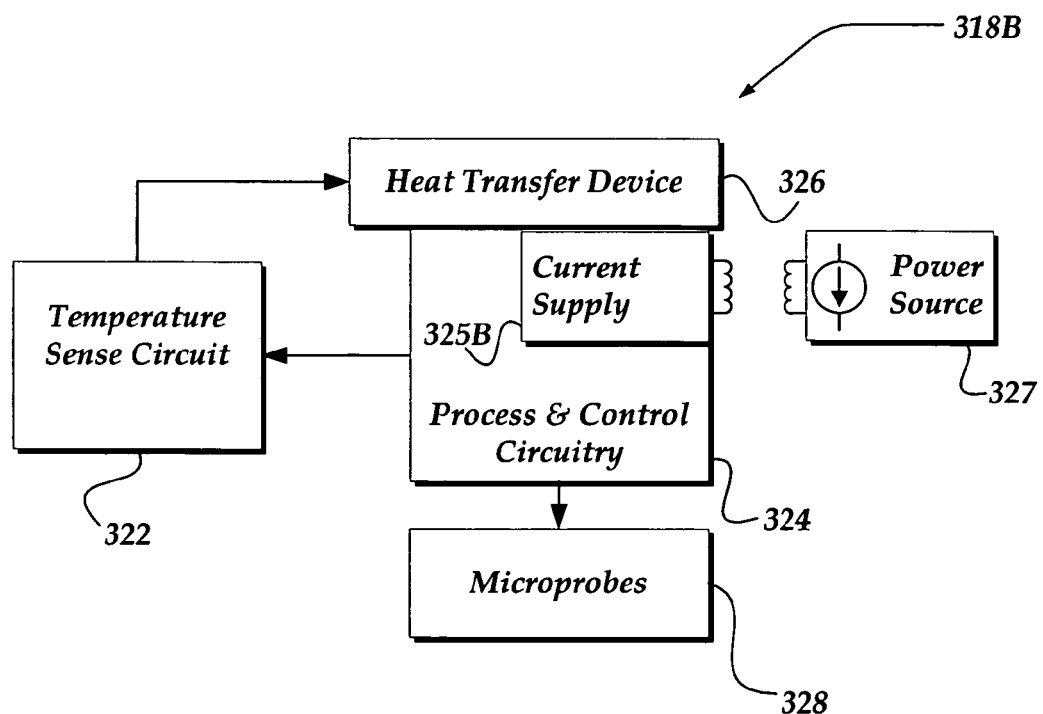

FIGS. 3A and 3B illustrate block diagrams of two embodiments of prosthetic retinal devices 318A and 318B. As shown, retinal devices 318A and 318B can include temperature sense circuit 322, process and control circuitry 324, heat transfer device 326, and microprobes 328. Process and control circuitry 324 includes in one embodiment current supply 325A and in another embodiment current supply 325B. Prosthetic retinal device 318B further includes power source 327.

Prosthetic retinal devices 318A and 318B may include circuitry for receiving and processing incident light information from an external source such as a camera, photoelectric sensor, and the like, and providing electrical signals to microprobes 328, which deliver the signals as electrical stimulation to the anterior surface of the retina. Prosthetic retinal devices 318A and 318B may further include multiplexing circuitry, mechanical activation circuitry, and the like, which may be incorporated in process and control circuitry 324. In one embodiment as shown in FIG. 3A, power may be provided to retinal device 318A through photosensitive sensors disposed on a top surface of the device from a laser beam along with the optical signals, a battery, a combination of multiple energy sources, and the like. Current supply 325A may provide a current as described below based on the energy source.

In another embodiment as shown in FIG. 3B, power may be provided to retinal device 318B through RF induction. Power source 327 may be an external power supply device that is arranged to provide power through RF induction to current supply 325B, which provide the current to process and control circuitry 324 based on the inductively provided power.

In one embodiment, prosthetic retinal devices 318A and 318B may be manufactured from a flexible semiconductor that is suited for positioning on the anterior surface of the retina. In another embodiment, retinal devices 318A and 318B may be suspended in the vitreous humor of the eye to avoid tearing and other damage to the retina. Additionally, to reduce a risk of infection, clotting, and the like, retinal devices 318A and 318B may be coated with heparin, teflon, and the like.

Prosthetic retinal devices 318A and 318B may include on their bottom surface microprobes 328 for delivering electrical signals and/or mechanical stimulation to an anterior surface of the retina. Microprobes 328 may include microbumps for delivering signals and/or MEMS for delivering mechanical stimulation. Microprobes 328 may be manufactured employing a durable and relatively inert material such as aluminum, titanium, platinum, platinum/iridium alloy, and the like. In part because the delivery of an electrical signal in a saline environment may increase the corrosion of bare metal over time, microprobes 328 may be coated with a material, such as teflon, resin, exposy, plastic, and the like. Additionally, the materials employed in the construction of microprobes 328 may take into consideration various parameters, including a temperature, a pH level, a salinity of vitreous humor filling the space in the eye.

Temperature sense circuit 322 may be arranged to monitor a temperature of prosthetic retinal devices 318A and 318B. In one embodiment, temperature sense circuit 322 may be integrated with process and control circuitry 324. In another embodiment, temperature sense circuit 322 may be provided on a second substrate that is attached to a first substrate that includes process and control circuitry 324. Temperature sense circuit 322 may further include circuitry that is arranged to activate heat transfer device 326, if a predetermined temperature is exceeded.

Heat transfer device 326 is arranged to receive heat from an upper surface of a first substrate that is disposed away from the anterior surface of the retina, and to dissipate the heat toward the iris or "front" end of the eye. In one embodiment, heat transfer device 326 may include a Peltier junction that is formed by the joining of two dissimilar semiconductor materials. A Peltier junction takes advantage of the Peltier effect between two dissimilar types of metals or semiconductors that transfer heat, if they are in physical contact and a current is passed through them. Each type of semiconductor has its own Peltier coefficient P. When the semiconductors are attached to each other and a current is applied, the heat energy "Q" that is transferred by the semiconductors may be expressed as follows:

$$Q=(P_A-P_B)*I_{AB},\qquad [1]$$

where $P_A$ is the Peltier coefficient of semiconductor A, $P_B$ is the Peltier coefficient of semiconductor B, and $I_{AB}$ is the current flowing from semiconductor A to semiconductor B. Accordingly, by reversing the direction of the current, the direction of heat transfer/exchange may be reversed.

Figure 4A:
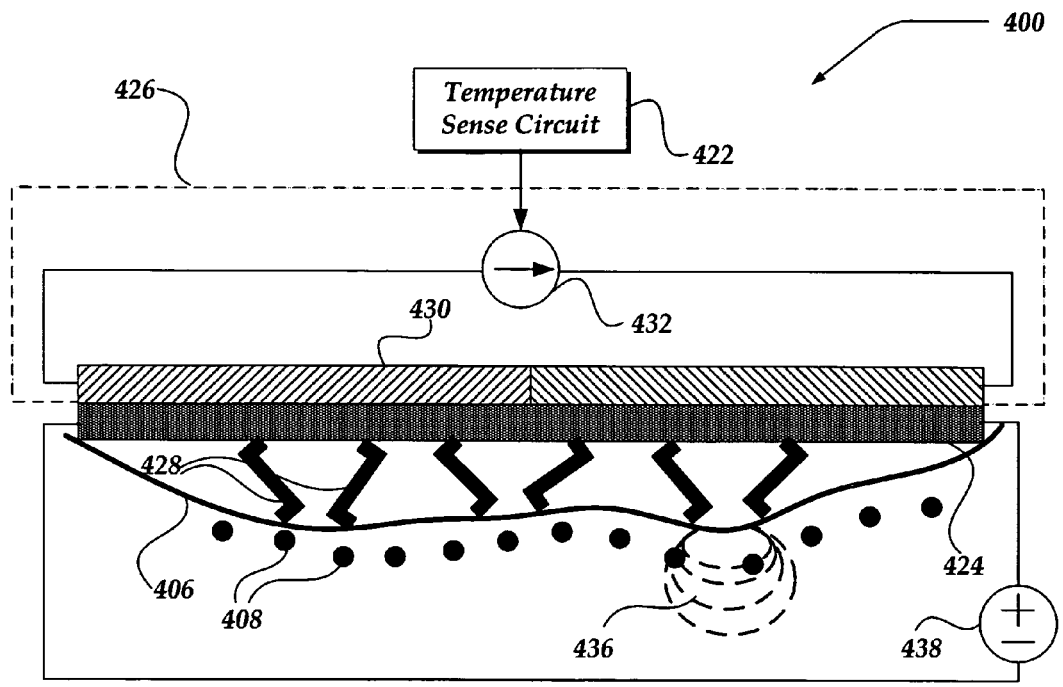
FIGS. 4A and 4B show block diagrams of two embodiments of a temperature controlled epiretinal prosthetic device positioned over the anterior surface of the retina.
Figure 4B:
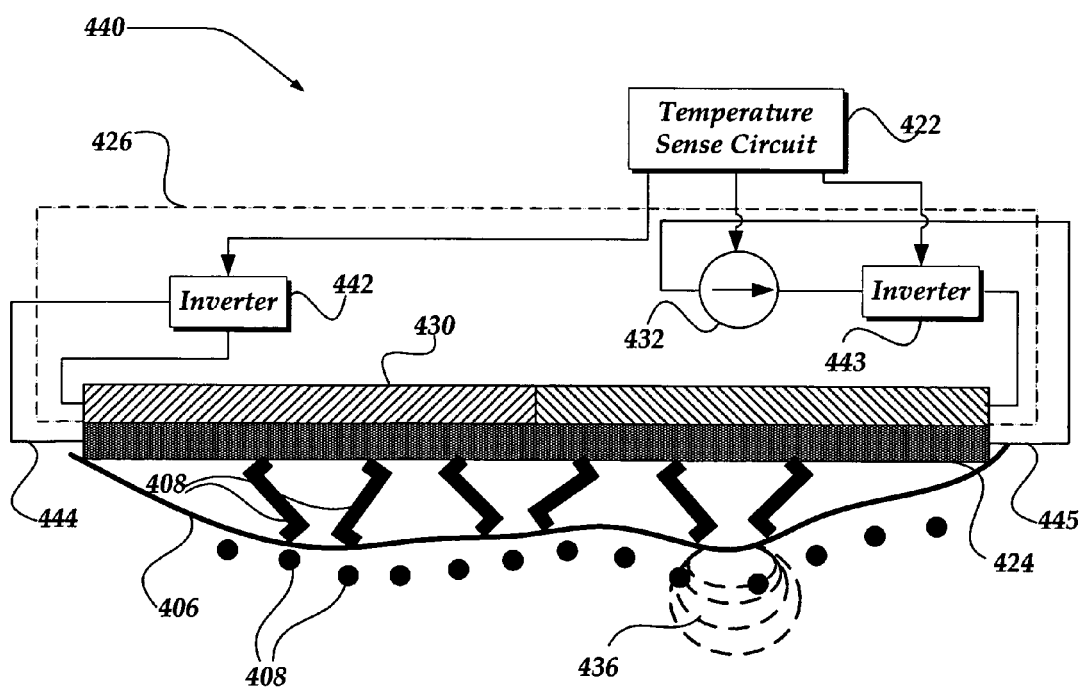

As described in more detail in FIGS. 4A and 4B, one embodiment of heat transfer device 326 may comprise a current supply for the heat pump that is separate from a power supply of process and control circuitry 324. In another embodiment, a supply current for process and control circuitry 324 may flow through the heat pump first, and the current may be reversed, if the predetermined temperature is exceeded resulting in heat to be withdrawn from process and control circuitry 324 and dissipated to vitreous humor in the direction of the iris or "front" end of the eye.

Because a density and a distribution of photosensitive cells (rods and cones) varies throughout the anterior surface of the retina, visual stimulation in a healthy eye may not be uniform across the same surface. Therefore, different types of prosthetic retinal devices 318A and 318B with varying microprobe densities may be implanted in different areas of the anterior surface of the retina.

FIG. 4A illustrates diagram 400 showing one embodiment of a temperature controlled prosthetic retinal device over the anterior surface of the retina 406. Diagram 400 includes temperature sense circuit 422, heat transfer device 426, process and control circuitry 424, microprobes 428, anterior surface of the retina 406, ganglion cells 408, electrical stimulation field 436, and voltage supply 438 for process and control circuitry 424. Heat transfer device 426 includes current supply 432, and Peltier junction 430.

As described above, microprobes 428 may be aligned with the bottom surface of process and control circuitry 424, engaging anterior surface of the retina 406, in an on-position. For optimum electrical stimulation, physical contact of each microprobe 428 with the anterior surface of retina 406 is preferred. Furthermore, the physical contact of microprobes 428 with the anterior surface of retina 406 may provide additional mechanical stimulation. Thus, different levels and types of stimulation may be accomplished depending on whether microprobes 428 are in contact with anterior surface of retina 406, a pressure of the contact by microprobes 428, and a level of stimulation current applied by microprobes 428.

Process and control circuitry 424 is arranged to receive optical stimulation signals, and to determine an amount of stimulation current and a pressure to be applied by microprobes 428. In one embodiment, an ambient light level and available power for process and control circuitry 424 may be used to determine a pressure level for contact between microprobes 428 and anterior surface of the retina 406. Accordingly, the pressure applied by each microprobe may be modified to achieve optimum stimulation without causing damage to the retina.

In addition, a randomly patterned duty-cycle may be applied to the electrical and mechanical stimulation. For example, once optimum positions of microprobes 428 and the amount of stimulation current is determined, the microprobes may be randomly disengaged from the retina and reengaged. Similarly, the electrical current may be duty-cycled with a random pattern generating an optimum amount of electrical field 436 for stimulating ganglion cells 408. Power for process and control circuitry 424 may be provided by voltage supply 438. In another embodiment, a current supply may provide power to process and control circuitry 424.

Heat transfer device 426 includes Peltier junction 430, which is arranged to be in thermal contact with process and control circuitry 424. In one embodiment, current source 432, which is controlled by temperature sense circuit 422, is arranged to provide supply current to Peltier junction 430. Temperature sense circuit 422 may be configured to monitor a temperature of process and control circuitry 424, and activate current source 432 (activating Peltier junction 430), if the temperature of process and control circuitry 424 exceeds a first predetermined limit.

Peltier junction 430 is arranged to transfer heat from a surface of process and control circuitry 424 to the vitreous humor by enabling the operation of the Peltier heat transfer effect. Peltier junction 430 may comprise a pair of metals, metal alloys, or semiconductors that transfer heat in one direction based on a polarity of the supply current passing through them. By transferring heat from the process and control circuitry 424 to the vitreous humor in a direction of the iris, Peltier junction 430 enables dissipation of the heat generated by the prosthetic retinal device away from the retina and thereby at least reducing a risk of infection or immune response to an elevated eye temperature. Peltier junction 430 is discussed in more detail below in conjunction with FIG. 5.

Temperature sense circuit 422 may be further arranged to deactivate current source 432 (deactivating Peltier junction 430), if the temperature of process and control circuitry 424 drops below a second predetermined limit. In one embodiment, the first predetermined limit and the second predetermined limit may be selected such that a hysteretic operation of Peltier junction 430 is enabled.

FIG. 4B illustrates diagram 440 showing another embodiment of a temperature controlled prosthetic retinal device over the anterior surface of retina 406. Diagram 440 includes temperature sense circuit 422, heat transfer device 426, process and control circuitry 424, microprobes 428, anterior surface of retina 406, ganglion cells 408, electrical stimulation field 436, and power connections 444 and 445 between process and control circuitry 424 and the heat transfer device. Heat transfer device 426 includes current supply 432, inverters 442 and 444, and Peltier junction 430.

Process and control circuitry 424 and microprobes 428 that are similarly named in FIG. 4A operate in substantially the same way as discussed above. The supply current from current source 432 may be provided to process and control circuitry 424 through inverters 442 and 443, and Peltier junction 430.

Because current source 432 is arranged to power process and control circuitry 424, current source 432 is activated during an entire operation of process and control circuitry 424. Accordingly, Peltier junction 430 is also active so long as process and control circuitry 424 operates. Temperature sense circuit 422 is arranged to control current source 432 and inverters 442 and 443, and enable a reversal of the supply current before and after process and control circuitry 424.

In a typical operation, current source 432 may provide a predetermined polarity of current, and inverters 442 and 443 may be in a non-inverting mode. Peltier junction 430 may transfer heat from vitreous humor to process and control circuitry 424 in this mode. Vitreous humor may have a characteristic temperature of approximately 96 degrees (1-2 degrees below body temperature). If a temperature of the process and control circuitry 424 is above the temperature of vitreous humor, but below the first predetermined limit, the heat transferred by Peltier junction 430 may help cool process and control circuitry 424.

If the temperature of process and control circuitry 424 exceeds the first predetermined limit, temperature sense circuit 422 may enable current source 432 to reverse the supply current resulting in a reversal of heat transfer direction of Peltier junction 430. Accordingly, heat pump may begin transferring heat from process and control circuitry 424 to vitreous humor in a direction of the iris as described before.

Because the supply current, which is provided to Peltier junction 430, is also provided to process and control circuitry 424 through power connections 444 and 445, a reversal of the supply current provided to process and control circuitry 424 may not be desired. A polarity of the supply current through process and control circuitry 424 may be maintained by activating inverters 442 and 443, which reverse the supply current before and after process and control circuitry 424.

If the temperature of process and control circuitry 424 drops below the second predetermined limit, an operation of Peltier junction 430 may be reversed yet again by reversing the supply current at current source 432. Inverters 442 and 443 may be deactivated substantially simultaneously with the reversal of the supply current.

In one embodiment, temperature sense circuit 422, heat transfer device 426, and process and control circuitry 424 may be implemented in the same microchip. In another embodiment, all three devices or a combination of two of the devices may be implemented in different microchips.

Figure 5:
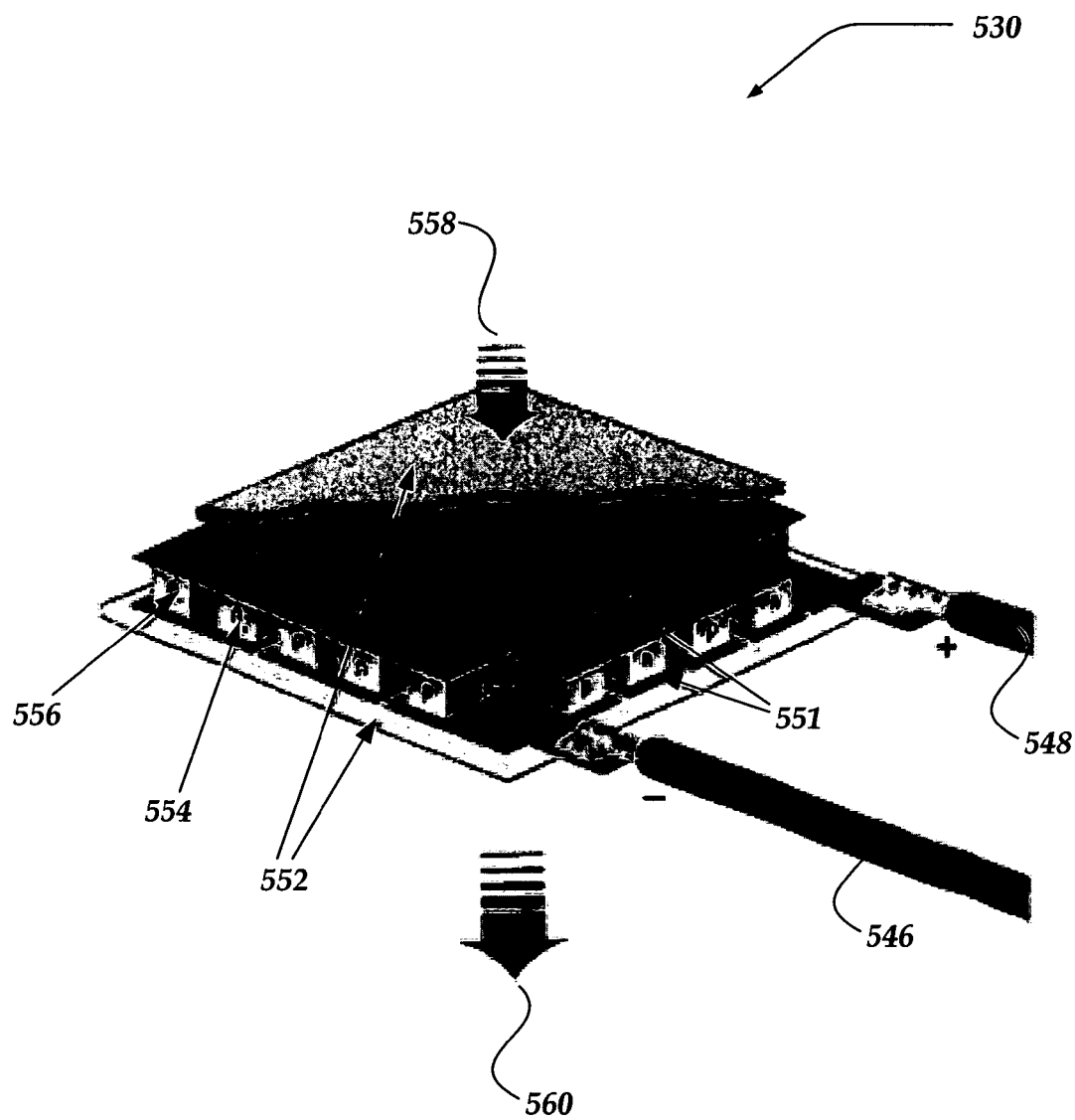
FIG. 5 illustrates one embodiment of a heat pump.

FIG. 5 illustrates an embodiment of heat pump 530. Heat pump 530 may be implemented as one embodiment of Peltier junction 430 in FIG. 4B. Heat pump 530 includes isolators 552, conductors 551, n-type semiconductors 554, p-type semiconductors 556, and power connections 546 and 548. FIG. 5 also shows direction of heat transfer 558 toward heat pump 530 and direction of heat transfer 560 away from heat pump 530, when a supply current flows from power connection 548 to power connection 546.

To implement the Peltier effect, heat pump 530 includes p-type and n-type semiconductors 556 and 554, which are mounted successively between conductors 551. P-type and n-type semiconductors 556 and 554 form p-n and n-p junctions that transfer heat in a direction determined by the direction of the supply current. Each junction is in thermal contact with conductors 551. When the supply current is applied, a temperature difference forms between conductors 551, which operate as radiators. According to the Peltier equation, the temperature difference may be expressed as follows:

$$T = \frac{3}{2}k(P_n - P_p)I_{np}, \qquad [2]$$

where $P_n$ is the Peltier coefficient of n-type semiconductor 554, $P_p$ is the Peltier coefficient of p-type semiconductor 556, and $I_{np}$ is the supply current flowing from n-type semiconductor 554 to p-type semiconductor 556. If the supply current is reversed to flow from p-type semiconductor 556 to n-type semiconductor 554, the same temperature difference may be obtained, but in a reverse direction.

Equations [1] and [2] above describing Peltier effect include constant coefficients that depend on characteristics of n-type semiconductor 554 and p-type semiconductor 556. Therefore, the constant coefficients may vary as new technology is developed and characteristics of semiconductor materials change with new manufacturing techniques. The Peltier effect, however, may continue to be employed to exploit characteristics of semiconductors to exchange heat even if the equations change.

Isolators 552 are arranged to provide protection for conductors 551, and to prevent unintentional electrical contact between heat pump 530 and another circuit. A variety of metal, metal alloy, and semiconductor pairs may be employed in heat pump 530. Fe-constantan, Cu—Ni, Pb-constantan are examples of metal-metal alloy pairs. $Bi_2Te_3$—$Bi_2Se_3$, $Bi_2Te_3$—$Sb_2Te_3$, CrAu—$Bi_2Te_3$, embedded into silicon, are examples of semiconductor pairs that may be used in a Peltier based heat pump. Implementation of heat pump 530 is, however, not limited to these materials.

Any metal, metal alloy, and semiconductor pair, which may provide a desired heat transfer efficiency may be utilized in heat pump 530.

An efficiency of heat pump 530 may be defined by a Coefficient of Performance (COP). COP may be expressed as:

$$COP = \frac{Q_1}{W}, \qquad [3]$$

where $Q_1$ is an amount of heat energy withdrawn from the environment by one side of heat pump 530, and W is an energy provided to heat pump 530 by the supply current. $Q_1$ and W are related through:

$$Q_2 = Q_1 + W, \qquad [4]$$

where $Q_2$ is an amount of heat energy dissipated to the environment by another side of heat 530. For example, at a COP of three, one Joule of energy provided to heat pump 530 may result in withdrawal of three Joules of heat energy by the cooling side, and dissipation four Joules of heat energy from the heating side.

Flow Charts

Figure 6:
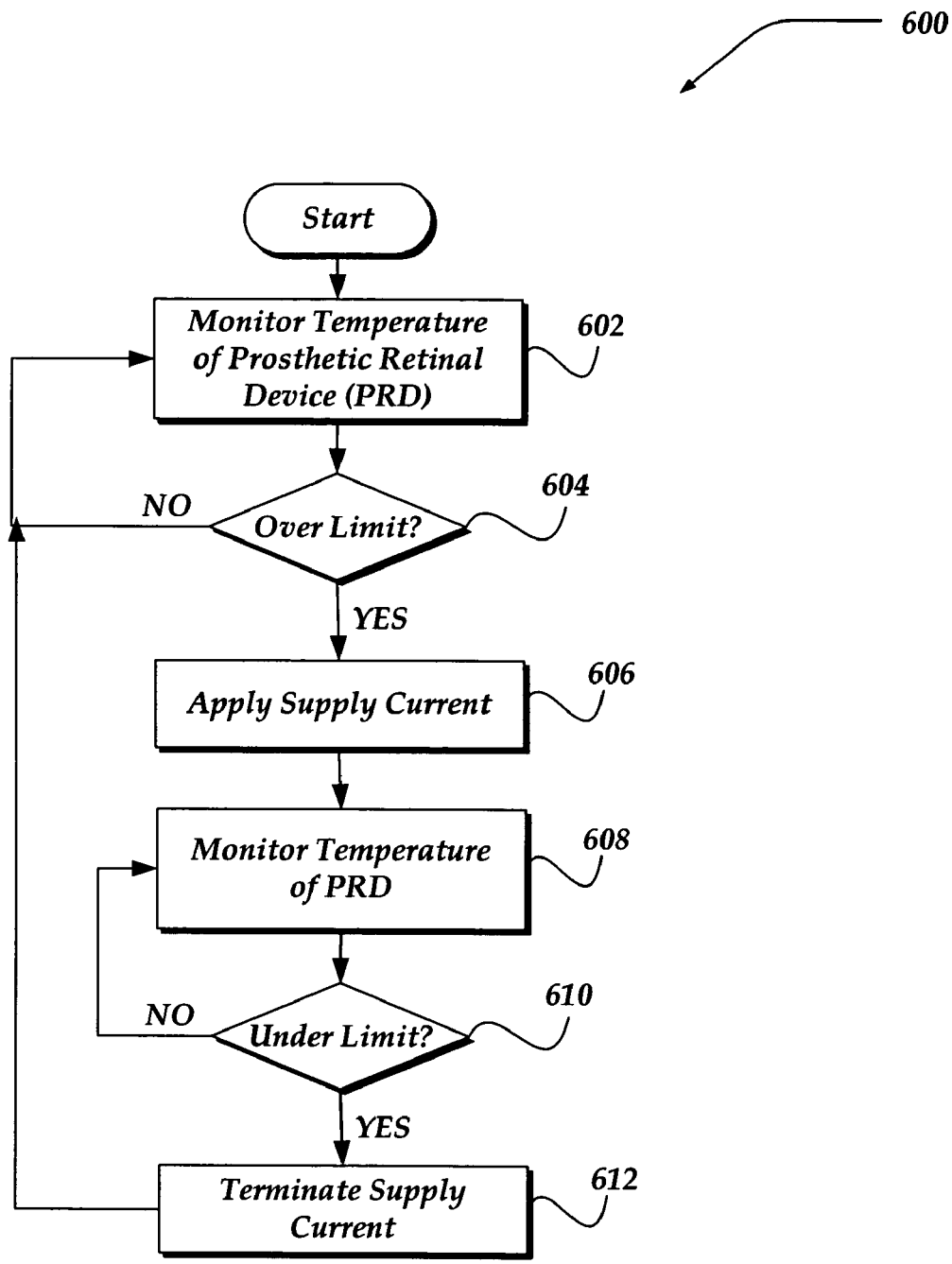
FIG. 6 shows a flow diagram generally showing a process for controlling a temperature of a retinal prosthetic device.

FIG. 6 illustrates a flow diagram generally showing process 600 for controlling a temperature of a prosthetic retinal device. Moving from a start block to block 602, a temperature of the prosthetic retinal device is monitored. Stepping to decision block 604, a determination is made as to whether a first predetermined temperature limit is exceeded. If false, the processing loops back to block 602 and performs substantially the same actions discussed above again.

However, if the determination at decision block 604 is affirmative, the process proceeds to block 606 where a heat transfer device is activated by providing a supply current to the device. As described previously, the heat transfer device may comprise two different kinds of metals or semiconductors that transfer heat, based on a direction of the supply current flowing through the heat pump. In one embodiment, the heat transfer device may be in thermal contact with a surface of the prosthetic retinal device, and the direction of the current may be selected such that heat is transferred from the surface of the retinal device towards the vitreous humor and front of the eye.

Next, the process proceeds to block 608 where the temperature of the prosthetic retinal device is monitored while the heat transfer device is in operation. The process advances to decision block 610 where a determination is made as to whether the temperature of the prosthetic retinal device has dropped below a second predetermined limit. If the determination is negative, processing loops back to block 608 for further monitoring of the temperature while the heat transfer device is operating.

However, if the decision at decision block 610 is affirmative, the process proceeds to block 612 where the heat transfer device is deactivated by terminating the supply current. Next, the process returns to block 602 and performs substantially the same actions as discussed above. Additionally, in one embodiment, the first predetermined limit and the second predetermined limit may be selected such that a heat transfer device operates in a hysteretic mode.

Figure 7:
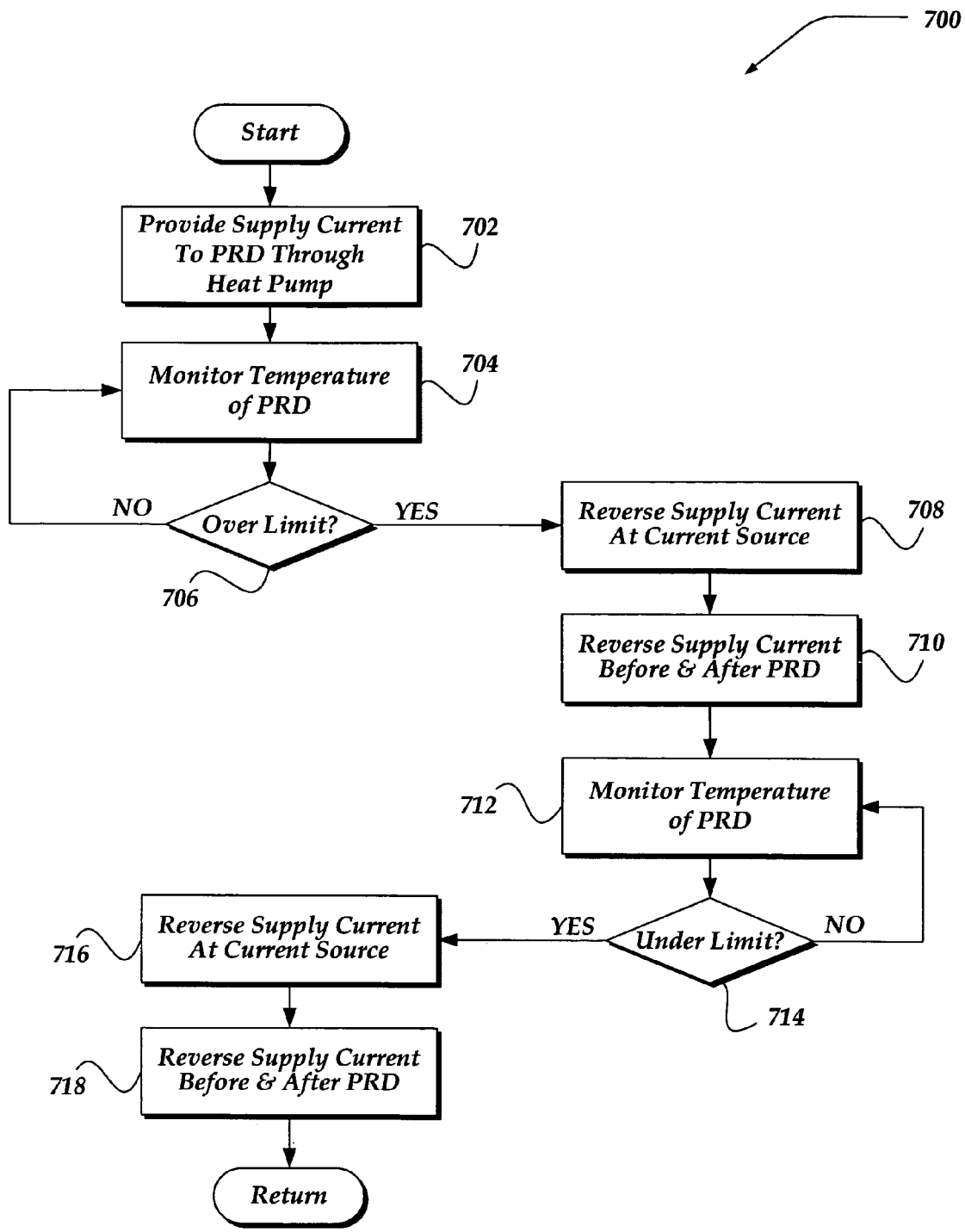
FIG. 7 illustrates a flow diagram generally showing a process for controlling a temperature control of a retinal prosthetic device, in accordance with the present invention.

FIG. 7 illustrates a flow diagram generally showing process 700 for controlling a temperature of a prosthetic retinal device. Moving from a start block, the process steps to block 702, where a supply current for the prosthetic retinal device is provided to a heat transfer device. In one embodiment, the heat transfer device and the retinal device may be formed on two substrates that are attached to each other. Providing the supply current for the retinal device through the heat transfer device may enable continuous transfer of heat while the retinal device is operating.

If a temperature of the retinal device is above a temperature of the vitreous humor, but below a first predetermined limit, the heat transfer device can transfer approximately the temperature of the vitreous humor to the retinal device and thereby providing a cooling effect on the anterior surface of the retina. Processing then proceeds to block 704 where a temperature of the retinal device is monitored and compared against a first predetermined limit.

Next, processing proceeds to decision block 706 where a determination is made as to whether the temperature of the retinal device exceeds the first predetermined limit. If the determination is negative, the process loops back to block 704 for further monitoring of the temperature. However, ff the determination at decision block 706 is affirmative, the process proceeds to block 708 where a polarity of the supply current is reversed at a current source that is included in the heat transfer device. In one embodiment, a temperature sense device such as temperature sense circuit 422 of FIG. 4B may control the current supply and reverse the supply current upon detection of the temperature exceeding the first predetermined limit.

Moving from block 708, the process steps to block 710 where the supply current is reversed before and after the retinal device. As described previously, the supply current may be provided to the retinal device through a heat transfer device. Two inverter devices such as inverters 442 and 443 of FIG. 4B may provide for reversal of supply current before and after the retinal device resulting in maintenance of a polarity of the supply current through the retinal device irregardless of the polarity of the supply current through a heat pump.

Next, the process proceeds to block 712 where the temperature of the retinal device is monitored and compared against a second predetermined limit. Processing then proceeds to decision block 714 where a decision is made as to whether the temperature of the retinal device drops below the second predetermined limit. If the determination is negative, the process returns to block 712 for further monitoring of the temperature. However, if the determination is affirmative, the process proceeds to block 716.

At block 716, the polarity of the supply current is again reversed at the current source. Processing then proceeds to block 718, where the inverters reverse the supply current before and after the retinal device to maintain the polarity of the current through the retinal device. Next, the process then returns to a calling process to perform further actions.

Each block of the flowchart illustrations discussed above, and combinations of blocks in the flowchart illustrations above, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor, provide steps for implementing the actions specified in the flowchart block or blocks.

Accordingly, blocks of the flowchart illustrations support combinations of means for performing the specified actions, combinations of steps for performing the specified actions and program instruction means for performing the specified actions. It will also be understood that each block of the flowchart illustrations, and combinations of blocks in the flowchart illustrations, can be implemented by special purpose hardware-based systems, which perform the specified actions or steps, or combinations of special purpose hardware and computer instructions.

The above specification, examples and data provide a description of the manufacture and use of the composition of the invention. Since many embodiments of the invention can be made without departing from the spirit and scope of the invention, the invention also resides in the claims hereinafter appended.

We claim:

1. A method for controlling a temperature of a prosthetic retinal device, comprising:
  sensing the temperature of a surface of the retinal device that is adapted for positioning towards a retina; and
  if the temperature is at least greater than a first predetermined limit, enabling the operation of a heat transfer device that is coupled to the retinal device, wherein the heat transfer device is arranged to transfer heat away from the retina during operation of the retinal device.

2. The method of claim 1, further comprising if the temperature is at least less than a second predetermined limit, deactivating the heat transfer device.

3. The method of claim 2, wherein the first predetermined limit and the second predetermined limit enable a hysteretic operation of the heat transfer device.

4. The method of claim 1, further comprising:
  providing a supply current to the heat transfer device by at least one of a current source circuit that is included in the heat transfer device and an external current source employing radio frequency (RF) induction.

5. The method of claim 1, further comprising:
  providing a supply current to the retinal device through the heat transfer device; and
  if the temperature is at least greater than the first predetermined limit, reversing the supply current to the heat transfer device.

6. The method of claim 5, further comprising:
  if the supply current to the heat transfer device is reversed, reversing the current between the heat transfer device and the retinal device, and reversing the current again between the retinal device and the heat transfer device.

7. A heat transfer device for controlling a temperature of a medical device adapted for disposition inside a human body, the heat transfer device comprising:
  a heat pump that is arranged to transfer of heat from the medical device away from tissue at an implantation location;
  a temperature sensor that senses the temperature of the medical device and enables control of the operation of the heat pump; and
  a first inverter and a second inverter that are arranged to reverse a supply current before and after the heat pump, so that the supply current to the medical device maintains substantially the same polarity during a reverse current operation of the heat pump.

8. The device of claim 7, further comprising a temperature sensor that is arranged to:
  sense a temperature of the medical device; and
  if the temperature exceeds a first predetermined limit, activate the heat pump; and
  if the temperature drops below a second predetermined limit, deactivate the heat pump; and
  a current source that is arranged to provide the supply current to the heat pump.

9. The device of claim 8, wherein the current source is arranged to provide the supply current to the medical device through the heat pump, and wherein the temperature sensor is arranged to reverse the supply current, if the first predetermined limit is exceeded.

10. The device of claim 8, wherein the current source is at least one of a current source circuit included in the heat transfer device or an external current source employing radio frequency (RF) induction.

11. The device of claim 7, wherein the heat pump is a Peltier junction that includes at least one of a $Bi_2Te_3$—$Bi_2Se_3$ pair, a $Bi_2Te_3$—$Sb_2Te_3$ pair, a CrAu pair, or a $Bi_2Te_3$ pair.

12. The device of claim 7, wherein the first inverter is arranged to reverse a polarity of the supply current between the heat transfer device and the process and control device, and the second inverter is arranged to reverse the polarity of the supply current between the process and control device and the heat transfer device, so that the supply current to the process and control device receives relatively the same polarity during a reverse current operation of the heat transfer device.

13. The device of claim 7, wherein a coefficient of performance of the heat transfer device is at least three.

14. The device of claim 7, further comprising a coating for at least a portion of the device, wherein the coating includes at least one of teflon, heparin, plastic, resin or epoxy.

15. The device of claim 7, further comprising:
  a process and control circuit that perform actions including:
    receiving light information; and
    enabling a current to stimulate a retina with at least one microprobe; and wherein the heat transfer device is coupled to the process and control circuit.

16. The device of claim 15, wherein the microprobe includes at least one Micro-Electromechanical System (MEMS).

17. The device of claim 15, wherein the process and control device is further arranged to determine at least one of the stimulation current or a pressure that is applied by the microprobe based, in part, on at least one of an ambient light level or an intra-ocular pressure.

18. The device of claim 15, wherein the microprobe is disengaged and re-engaged from contact with an anterior surface of the retina based, in part, on a duty-cycle.

19. The device of claim 15, wherein the stimulation current is duty-cycled based on a predetermined rate.

20. The device of claim 15, wherein the retinal device is formed from at least one of a substantially flexible material or a substantially curved material.

21. The device of claim 15, further comprising a receiver for receiving power from a remote source, wherein the receiver employs at least one of coherent light or a Radio Frequency (RF) signal to receive power.

* * * * *